United States Patent [19]

Eberle et al.

[11] Patent Number: 5,413,906
[45] Date of Patent: May 9, 1995

[54] METHOD OF DETERMINING POLYMERASE ACTIVITY

[75] Inventors: Josef Eberle, Munich; Rudolf Seibl, Penzburg; Christoph Kessler, Dorfen; Bernhard Konig, Berg, all of Germany

[73] Assignee: Boehringer Mannheim GmbH, Mannheim, Germany

[21] Appl. No.: 974,595

[22] PCT Filed: May 31, 1991

[86] PCT No.: PCT/EP91/01016

§ 371 Date: Mar. 19, 1993

§ 102(e) Date: Mar. 19, 1993

[87] PCT Pub. No.: WO92/04467

PCT Pub. Date: Mar. 19, 1992

[30] Foreign Application Priority Data

Aug. 31, 1990 [DE] Germany ............... 40 27 616.3

[51] Int. Cl.⁶ .................. C12Q 1/68; C12Q 1/70; C12P 19/34
[52] U.S. Cl. .......................... 435/5; 435/6; 435/91.1; 435/7.72; 435/15
[58] Field of Search .......... 435/6, 5, 91.1, 7.72, 435/15; 536/22.1, 26.6

[56] References Cited

U.S. PATENT DOCUMENTS 4,683,195 7/1987 Mullis et al. .............. 435/6

OTHER PUBLICATIONS

Advani et al. J. Clin. Microb. 27(7) 1453-1455 (1989).
Lee et al. J. Clin. Microb. 25(9) 1717-1721 (1987).
Day et al. Biochem. Journal 267:119-123 (1990).
Arias et al. J. Biol. Chem. 264(6):3223-3229 (1989).

*Primary Examiner*—Margaret Parr
*Assistant Examiner*—Kenneth R. Horlick
*Attorney, Agent, or Firm*—Nikaido, Marmelstein, Murray & Oram

[57] ABSTRACT

Method of determining polymerase activity by incubating the polymerase with a template nucleic acid, one detectable mononucleoside triphosphate and one immobilizable nucleoside triphosphate, binding the immobilizable nucleotides to a solid phase and detecting the bound detectable nucleotides and tests based thereon.

14 Claims, 2 Drawing Sheets

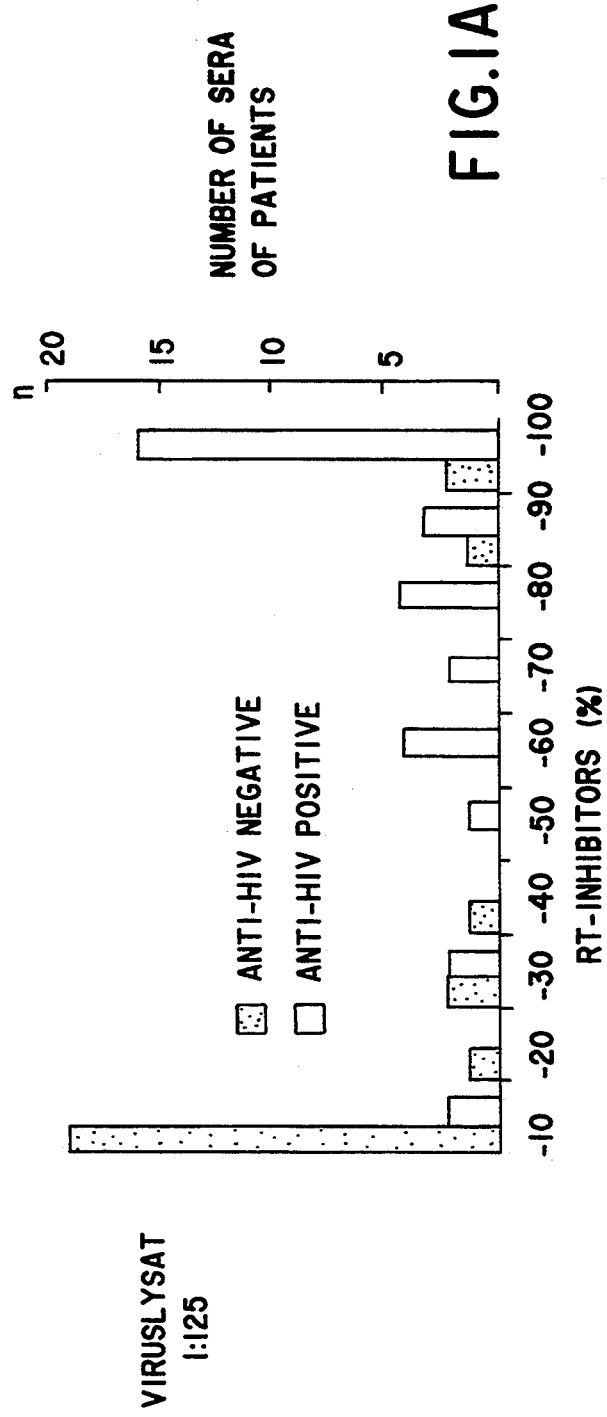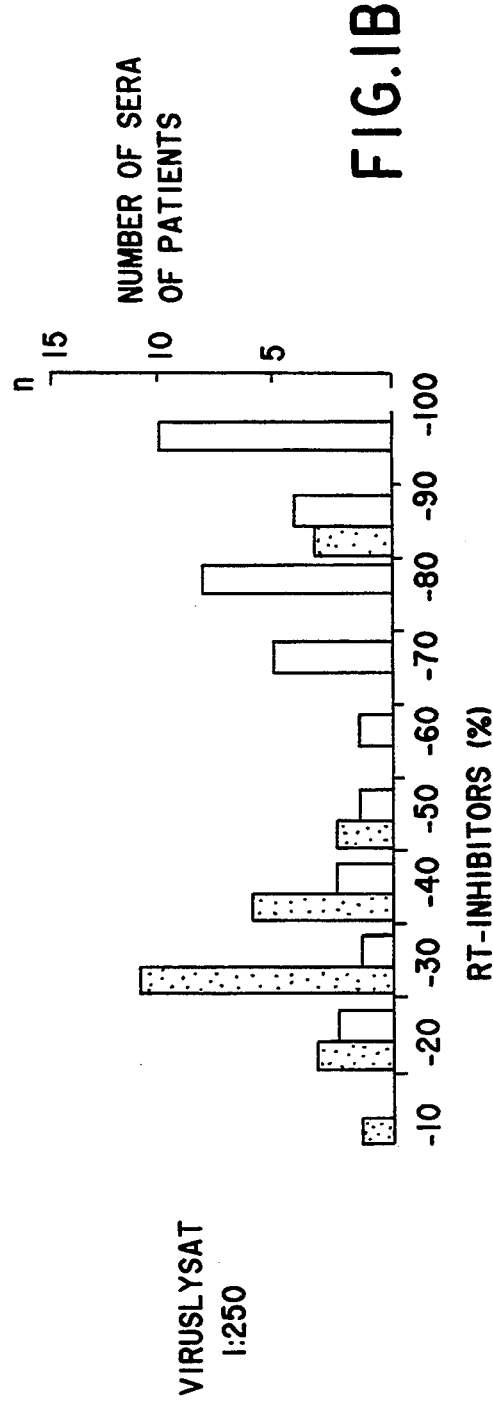

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

GTCCCTGTTC GGGCGCCA                                                    1 8

METHOD OF DETERMINING POLYMERASE ACTIVITY

The invention adresses a method of determining polymerase activity, a reagent and a reagent kit for implementing said method and the use of said method for the detection of HIV. The invention also addresses a method of determining the inhibitory effect of substances on polymerase activities, a method of detecting antibodies to polymerase and a method of detecting promoter sequences.

Polymerases are enzymes of fundamental importance to living beings. They are responsible, for example, for the synthesis of nucleic acids and their transformation into other nucleic acids necessary for the synthesis of proteins. Polymerases are, therefore, found in all types of cells including, for example, bacteria. Even many viruses code for their own polymerases. One special representative is a polymerase known as reverse transcriptase (RT).

With the discovery of human pathogenic retroviruses in the last decade (Science (1983), 220:868–871, Proc. Natl. Acad. Sci. USA (1980), 77:7415–7419 and Biochem. Biophys. Res. Comm. (1984), 121:126–133), the detection of the reverse transcriptase (RT), being the typical key enzyme of this virus family, has gained more and more importance. Numerous improvements of the method of determining RT-activity have since been described (Virology (1985) 147:326–335). RT-tests are commonly used in the following 3 situations:

1. characterizing a newly isolated virus as a retrovirus and to differentiate between different retroviruses,
2. determining the success of a virus isolation from test material of a subject known to be infected with a retrovirus or a subject that may be infected and
3. clarifying the in-vitro effectivity of chemotherapeutic agents against these enzymatic functions, that are essential for retroviruses.

With respect to the first two of the above mentioned fields of application, the known RT-test is limited in that it involves tedious sample preparation (ultracentrifugation or PEG precipitation, sensitivity may be too low otherwise); as regards the second field of application, the competition by sensitive, less expensive and simpler methods of antigen detection (ELISA); what limits all three of the above fields of application is the fact that conventional RT-tests use isotope nucleotides thus making special demands on the laboratory (equipment, authorization, personnel, waste disposal).

All methods of detecting enzyme activity of a reverse transcriptase, particularly reverse transcriptase of HIV, that are known from literature are based on assays, where a primer, which is complementary to a partial sequence of a template, is extended by incorporating labelled nucleotides. Non-incorporated nucleotides are usually separated from the extended primer that is bound to the template via hydrogen bonds by precipitating the polymer with the aid of trichloroacetic acid or ethanol followed by a filtration procedure or by adsorption of the polymer to a membrane filter having a positively charged surface (e.g. to DEAE, as described in Journal of Virological Methods 19 (1988), 161–168); or by employing any other method suitable to separate a negatively charged polymer from a negatively charged monomer. These measures are very tedious and require additional handling steps.

WO 90/06373 describes a method which uses immobilized nucleic acids as template nucleic acids. A drawback of this method is that sufficient specific immobilization of this template nucleic acid without obstructing the access for enzymes is not possible. The method can, hence, be limited by the available amount of reactive template nucleic acids. Further, the method produces a large number of different nucleic acids for which the binding to the solid phase via the template-DNA greatly varies as a consequence of different hybridisation conditions. Moreover, reactions at a solid phase generally exhibit poorer kinetics than do reactions in solutions.

Moreover, it has been found that for the quantitative determination of HIV-particles, immunoassays for the detection of HIV-antigens are not reliable (New England Journal of Medicine(1989). Vol. 321, 24, 1673–1675).

J. Clin. Mircobiology 27 (1989), 7, 1453–1455 and AIDS Research and Human Retroviruses 5 (1989), 535–540 disclose a method of detecting antibodies to HIV-RT which is based on the determination of polymerase activity in the presence of antibodies to HIV. The radioactively labelled nucleic acids synthesized by the polymerase are immobilized at membranes in a non-specific manner. This method is also very tedious.

It was, hence, an object of the invention to provide a quick, simple, more reliable and more sensitive test for polymerase activity. This object has been accomplished by the invention.

The subject matter of the invention is a method of determining polymerase activity comprising the following steps:

incubating a polymerase-containing sample with a template nucleic acid and a detectable mononucleoside triphosphate, separating the synthesized nucleic acid from the detectable mononucleoside triphosphate and detecting the detectable nucleotides contained in the nucleic acids whereby the incubating mixture contains, in addition, an immobilizable mononucleoside triphosphate and the incubating mixture is brought into contact with the solid phase, said solid phase binding selectively and essentially completely the immobilizable mononucleoside triphosphate and the nucleic acids in which the immobilizable nucleotide is incorporated.

Further subject matters of the invention include reagents for implementing the method, a method of determining the inhibitory effect of substances on polymerase activity, a method of detecting antibodies to polymerase and a method of detecting promoter sequences.

Polymerase activity is understood to be the enzymatic activity of polymerases to polymerize mononucleoside triphosphates into a nucleotide sequence with the aid of a template nucleic acid. In this process, the mononucleotides are added to a nucleic acid sequence and incorporated into a nucleic acid strand complementary to a nucleic acid sequence. Depending on the polymerase, the resulting product is either a single-stranded or a double-stranded nucleic acid.

There are several types of polymerases which can be determined with the method of the invention. These polymerases are distinguished according to substrate and/or polymerization product. Examples include DNA-dependent RNA-polymerases (type I), such as T3-, T7- or E.coli-RNA-polymerase, DNA-dependent DNA-polymerases (type II), such as Klenow-fragment, RNA-dependent DNA-polymerases (type III), such as reverse transcriptase, and RNA-dependent RNA-polymerases (type IV), such as Qβ- and Picornavirus-polymerase. In the method of the invention, for example, viral reverse transcriptases, especially HIV-reverse transcriptase are used as analytes.

In the present invention the term template nucleic acids refers to nucleic acids which function as a substrate of the polymerase or the type of polymerase to be determined. Substrates for type I and type II are therefore deoxyribonucleic acids, substrates for type III and type IV are ribonucleic acids. A deoxyribonucleic acid may also serve as a substrate for type III. To make a distinction from type II, however, the preferred substrate is a ribonucleic acid.

As regards type II and III polymerases, it is possible to use heteropolymeric as well as homopolymeric nucleic acids as template nucleic acids. The measurement of in-vitro activity of type II or type III-polymerases usually requires the addition of primers.

Testing for type I-polymerases requires the use of a nucleic acid having a corresponding specific promoter such as the lac-promoter from *E. coli* for *E.coli* RNA-polymerase or promoters from T7-phages for T7-RNA-polymerase (Chainberlin and Ryan (1982). The Enzyme, Vol. XV, pp 87–108, ). Conversely, the detection of a specific promoter requires a specific polymerase.

The template nucleic acids for the determination of type IV-polymerases also have specific primer structures including terminal-bound proteins, certain secondary structures, etc. These structures depend on the polymerase and are known to the expert.

Mononucleoside triphosphates are the triphosphates of nucleosides containing either natural bases such as adenine, guanine, cytosine and uracil or thymine or artificial bases such as aza- and deaza-analogs of the natural bases, for example, 7-deaza-2'deoxyguanosine triphosphate. The term mononucleoside triphosphates refers to monoribonucleoside phosphates or monodeoxyribonucleoside triphosphates depending on the type of polymerase activity to be determined. Types I and IV require ribonucleotides, whereas types II and III require deoxyribonnucleotides. As regards the reverse transcriptase, it is possible to use both ribo-as well as deoxyribonucleotides. Deoxyribonucleotides are, however, preferred since the combination of deoxyribonucleotides with ribonucleic acids as template nucleic acids is specific to type III-polymerases.

Detectable mononucleoside triphosphates as defined by the invention are modified triphosphates. This modification allows a selective detection of the mononucleotides in the presence of natural mononucleotides, for example, in photometric, fluorometric, radiometric, enzymatic or immunological reactions. In a preferred manner, the mononucleoside triphosphate has a covalently bound non-radioactive chemical group. This may be a dye, a fluorescent label or a component of an immunologic reaction such as an antigen, antibody or hapten. Haptens are preferred, with digoxigenin being particularly preferred, because of its high sensitivity. In this context, we refer to the disclosure of EP-A-0 324 474 and EP-A-0 254 090.

In addition to the detectable mononucleoside triphosphate, the present invention also uses an immobilizable mononucleoside triphosphate. Immobilization of these mononucleotides can be achieved, for example, by covalently bound chemical groups which have a specific affinity for a solid phase. In a preferred manner, the chemical group is one of the binding partners of a specific combination. Such combinations are, for example, antigen-antibody, hapten-antibody, antibody-antibody, vitamin-binding protein, cofactor-enzyme and sugar-binding protein (lectin). A particularly preferred combination is vitamin-binding protein, especially biotin-avidin or biotin-streptavidin, biotin representing the chemical group of the mononucleotide bound via a linker. In order to obtain the results intended by the invention, the immobilizable mononucleoside triphosphate should be different and distinguishable from the detectable mononucleotide. The method is then considerably less susceptible to interference and less dependent from the amount of incorporated nucleotide as compared to the case where the mononucleotides are identical. As has been shown for biotin- and digoxigenin-nucleotides, the respective polymerase must accept the detectable and immobilizable mononucleoside triphosphate as a substrate.

Any liquid to be tested for its contents of polymerases is a suitable sample for the method of the invention. The method is suitable to determine polymerases in liquids in preferred concentrations of $10^{-12}$ to $10^{-8}$ mol/l, particularly preferred $8 \times 10^{-11}$ to $8 \times 10^{-10}$ mol/l (determined for RT). Solutions with such concentrations are, for example, obtained when isolating polymerases but are also found in lysates of viruses and bacteria or in supernatants of cell cultures. The lysates can be both lysates from tissue and from body liquids such as blood. Further isolation of the polymerase from lysates is not ncessary. The preparation of such samples is, for example, described in Virology (1985) 147:326; PNAS (1980) 77, 7415. Due to its high sensitivity, it is an advantage of the method that in most cases tedious concentration steps are no longer required.

In a first step of the invention, a template nucleic acid and at least one detectable mononucleoside triphosphate and one immobilizable mononucleoside triphosphate are added to the sample. If a polymerase is to be detected whose activity depends upon the presence of a primer, the primer used is an oligonucleotide or a polynucleotide, which is shorter than the template nucleic acid and complementary to a part of the template nucleic acid and which, by means of the polymerase, can be extended by a strand segment that is complementary to the template nucleic acid. The prevailing conditions must allow the polymerase to fully develop its enzymatic activities. These conditions vary depending on the polymerase but are known to the expert. They include, for example, the addition of a pH buffer to stabilize the pH value near the activity maximum of the polymerase or, for example, the presence of cations necessary for the respective polymerase activity. It is also possible to add detergents such as Triton X 100 or complex former such as EDTA. The optimum temperature is also known to the expert. The detection of thermophilic polymerases, e.g. Taq-DNA-polymerase of EP-A-0 258 017, can, for example, be carried out at elevated temperatures. If the template nucleic acid is a homopolymer, the mononucleoside triphosphate must comprise a nucleotide which is complementary to the nucleotide of the template nucleic acid. If polyadenylate is used as a template nucleic acid, the triphosphate preferably contains a thymine or uracil residue since the latter can be used to form a nucleic acid strand that is complementary to polyadenylate.

Moreover, the incubating solution can also contain the non-detectable and/or non-immobilizable mononucleoside triphosphate which is the basis for the detectable and/or the immobilizable mononucleoside triphosphate.

If the template nucleic acid is a copolymer consisting of all 4 mononucleotides, the incubating solution must contain each of the corresponding 4 mononucleoside triphosphates, regardless of its form, be it detectable, immobilizable or non-detectable or non-immobilizable. In a preferred case, the concentration of the four mononucleoside triphosphates is approximately the same and a part of a triphosphate is present in its immobilizable form and another part of the same triphosphate or of another triphosphate is present in its detectable form. The preferred total concentration of each triphosphate is at 0.0001 to 10 mmol/l, a particularly preferred concentration ranges between 0.001 to 10 mmol/l.

The incubation period for the detection of the reverse transcriptase in a concentration of appr. $10^{-11}$ mol/l can be terminated after appr. 90 min at 35° C. Smaller quantities up to $10^{-12}$ mol/l can be detected when the incubating period is extended to 24 hours.

Incubation may be carried out in any available pre-incubating vessel, for example a microtiter plate or a tube or vial but also when already in contact with a solid phase to which the immobilizable mononucleoside triphosphate or the nucleic acids containing the latter are able to bind. In a preferred case, the pre-incubating vessel already contains said solid phase, and can, hence, bind said compositions. Transfer into another vessel for incubation with the solid phase is then no longer required.

During a separation step, the nucleic acids, which may have been produced due to the polymerase activities and contain at least one incorporated immobilizable and at least one incorporated detectable mononucleotide, are bound to a solid phase and the liquid phase is removed.

The solid phase to which the immobilized mononucleoside triphosphate and the nucleic acids, in which said mononucleoside triphosphate was incorporated, are bound contains the other binding partner. In a particularly preferred manner, the solid phase is coated with streptavidin. The solid phase may be present in the form of a container or as beads. Typical and preferred vessels are cuvettes and microtiter plates. When beads are used, immobilization requires a separate vessel to contain the incubation mixture unless the preincubation vessel is used.

The solid phase must be able to preferably bind 90% or more of the total quantity of immobilizable mononucleoside triphosphate and nucleic acid with the immobilizable nucleotide incorporated therein contained in the incubating solution. For this purpose, the solid phase should contain at least 90%, preferably more binding sites than the originally available quantity of immobilizable mononucleotide. Since this quantity is known, the expert can easily determine the necessary surface or, conversely, by measuring the binding ability of the solid phase with respect to solutions containing different quantities of mononucleotides, it is possible to determine the largest possible quantity of mononucleotide that is bound by the solid phase. It does, however, not interfere with the determination if the amount of binding sites at the solid phase exceeds the quantity of mononucleotide. Streptavidin-coated solid phases as described in EP-A-0 344578 are particularly preferred solid phases. The use of a specific binding pair ensures that only a minor amount of non specifically bound, labelled mononucleoside triphosphate is present. Due to the affinity of the above described binding partners, especially biotin/streptavidin, the immobilizable mononucleotides are almost completely bound.

In the case of biotin/streptavidin, incubation of the solid phase with the incubation mixture at 35° C. lasts less than 2 hours. The liquid is then separated from the solid phase, for example by means of decanting, pipetting or drawing off. Non-incorporated detectable mononucleoside triphosphate is thus separated from the immobilized detectable mononucleotide. To ensure complete separation, a post-treatment with a wash solution may follow. Due the firm binding of the nucleic acids containing incorporated immobilizable nucleotides to the solid phase, there is no significant washing-out of the immobilized nucleic acids. Possible wash solutions include, for example, simple salt solution such as buffered and unbuffered sodium chloride solutions. It is, hence, not necessary to use wash solutions that maintain hybridization of the template nucleic acids to the newly formed nucleic acids, as is required in prior art.

Subsequently, the nucleic acids bound to the solid phase are determined with the aid of the also incorporated detectable nucleotides. The determination depends upon the type of detectable nucleotide used. In a preferred case, where the detectable group of the mononucleotide is one component of an immunological reaction, the solid phase is reacted with the other component of said immunological reaction. This second component is preferably labelled, e.g. with an enzyme or a fluorescent label. Particulary preferred is labelling with enzymes such as horse-radish peroxidase (POD), alkaline phosphatase or $\beta$-galactosidase. In the preferred case the first component is a hapten and the second component is a labelled antibody to this hapten. In this connection we refer to WO 89/06698 and EP-A-0 209 875. If the label is a direct label such as a dye or a fluorescent dye, the detectable mononucleotide can be determined directly either by means of visual or automated analysis, in the latter case with a photometer or a fluorometer. If an enzyme label is used, the solid phase is reacted with a substrate for this enzyme and the reaction is photometrically or fluorometrically monitored.

In the method of the invention, the quantity or the presence of a polymerase or a type of polymerase can be understood from the quantity or the presence of detectable mononucleotide at the solid phase. A quantitative analysis can be based on a calibration curve obtained with samples whose contents of polymerases is known.

If the conditions under which the individual polymerases and/or types of polymerases incorporate detectable and immobilizable mononucleotide vary, it is possible to discriminate between individual polymerases and between types of polymerases. The method of the invention is, hence, a selective procedure allowing, for example, the determination of polymerases of the one type in the presence of polymerases of the other type.

It is an advantage of the method in accordance with the invention that the labelled nucleic acid can be separated from the labelled mononucleoside triphosphate in a very simple and complete manner. Moreover, this procedure can be carried out in one single vessel. Transfers into different vessels are no longer required. The use of a non-radioactive assay method has further advantages: the reaction requires less instrumentation and it is easier to automate and allows parallel determinations of numerous samples, for example in microtiter plates. The method is highly specific since only immobilizable nucleotides and nucleic acids containing the latter are bound to the solid phase. Samples with a less-than-maximum degree of puritiy are, hence, also acceptable for the method of the invention. Even determination in the presence of bacteria is, for example, possible. It is not necessary to separate the newly formed strand from the template nucleic acid when a hapten such as digoxigenin is used as the detectable mononucleotide. The method of the invention is considerably more reliable since the length of the product of the polymerase reaction has less impact on the result than in the case where only one modified mononucleotide is used. When differently modified mononucleotides are used, the amount of immobilizable mononucleotide can be kept low in favor of a quantitative specific binding to the solid phase whereas the amount of detectable mononucleotide can be kept comparatively high for a higher sensitivity.

In a preferred embodiment of the method of determining reverse transcriptase, the sample is reacted with polyadenylate as a template nucleic acid, biotinylated dUTP (EP-A-0 063 879) as immobilizable and digoxigenin-labelled dUTP (WO 89/06698) as detectable mononucleoside triphosphate and oligodT as a primer. After incubating at appr. 35° C. for 90 min., the mixture is transferred into a streptavidin-coated cuvette. After incubating for appr. 60 min, the liquid is discarded and the cuvette is rinsed with a wash solution. Then, a solution of POD-labelled antibodies to digoxigenin is added. After a period of appr. 60 min, the liquid is again discarded and the cuvette is rinsed once more. Then, an ABTS ® solution is added and the coloration is measured at 405 nm.

Another subject matter of the invention is a reagent for use in the method of the invention and a template nucleic acid containing at least one detectable and at least one immobilizable mononucleoside triphosphate. The reagent is preferably free of polymerase. The detectable and the immobilizable mononucleoside triphosphate are different compounds based either on the same mononucleotide, e.g. uridine, or on different mononucleotides, e.g. adenosine (immobilizable) and uridine (detectable). If the template nucleic acid is a homopolymeric nucleic acid, e.g. polyadenylate, only one type of mononucleotides is required for the detectable and immobilizable mononucleoside triphosphate, i.e. the one containing the base (in this example uridine or thymidine) which is complementary to the nucleotide of the nucleic acid. If the template nucleic acid contains all the natural bases, the respective complementary mononucleotides must be present as triphosphates. In a preferred manner, the reagent also contains additives including water as a solvent, pH buffer substances, detergents, stabilizers or co-factors for the polymerase. A pH buffer substance is included to ensure a pH, alter adding the reagent to the sample, at which the polymerase to be detected, if present, is expected to be active.

The reagent in the form of an aqueous solution contains the above ingredients at the following concentrations:

| template nucleic acid | 0.1 | to 2000 | µg/ml |
|---|---|---|---|
| mononucleoside triphosphate | 0.0001 | to 10 | mmol/l |
| (total) preferably | 0.001 | to 10 | mmol/l |
| detectable mononucleotide | 0.0001 | to 10 | mmol/l |
| preferably | 0.001 | to 1 | mmol/l |
| immobilizable mononucleotide | 0.0001 µmol/l | to 0.1 | mmol/l |

If a primer is required, it should be present at a concentration of 10 ng/ml to 10 mg/ml, or preferably at a concentration of 10–2000 µg/ml. If biotin-dUTP is used as an immobilizable mononucleotide and digoxigenin-dUTP as a detectable mononucleotide, said two substances are used in the reaction at a molar ratio of 1:1 to 1:50000: for a reverse transcriptase the preferred molar ratio is 1:5 to 1:50, particularly preferred 1:10 to 1:30 (bio:dig). If nucleotides are used which are modified in a different way, an expert can optimize the values accordingly. The values can also be optimized in dependency upon the polymerase activity and the number of binding sites at the wall. Further, the reagent can also be used in the form of a concentrated solution which has to be diluted prior to use. Storage as a lyophilisate is also possible. In the latter case, the reagent is reconstituted with the aid of a solution.

Yet another subject manner of the invention is a reagent kit for the detection of polymerase activity. The kit contains the following in separate containers:
  template nucleic acid, at least one detectable and at least one immobilizable mononucleoside triphosphate
  a vessel to selectively and essentially completely bind the immobilizable mononucleotide, and
  wash solutions If necessary, a primer is included in the reagent kit (preferably in a mixture with the template nucleic acid). Aside from this reagent, the kit further contains a vessel necessary for carrying out the method and a wash solution. Moreover, a preferred embodiment of the kit contains reagents for the detection of the detectable mononucleotide. If, for example, an immunological combination for binding a label to the detectable mononucleotide is used, this kit provides the corresponding labelled partner of the component of the immunological combination which is bound to the detectable mononucleotide. When an enzymatic label is used, the kit also comes with an enzyme substrate and, if necessary, the required pH buffer substances. It is an advantage of the reagent kit of the invention that all reagents are stable and require relatively little storage space and their use and application is much easier as compared to reagents known in prior art.

A preferred embodiment of a reagent kit contains:
a) a container with template nucleic acid, digoxigenin-labelled mononucleoside triphosphate, biotin-labelled mononucleoside triphosphate, pH-buffer, detergent, complex former, co-factors, salts and anti-oxidizing agents
b) streptavidin-coated cuvette, tube, pellets or microtiter plate
c) wash solution
d) solution of a POD-labelled antibody to digoxigenin
e) A POD substrate, for example, 2,2'-azino-bis-13-ethylbenzothiazoline-6-sulfate] (ABTS ®) in buffer solution For the detection of type II or type III polymerases a), in a preferred manner, also contains a primer. All components of the reagent kit are stable, have extended storage stability, and both their manufacture and disposal are inexpensive and simple.

The method of the invention for detecting a polymerase activity can be employed in any field where such a polymerase activity reveals information on the composition of a sample. This is the case, for example, in the detection of polymerases in samples such as body fluids or processed enzyme isolates, further in the detection of polymerase-containing micro-organisms, particularly bacteria and viruses to characerize unknown polymerases or micro-organisms and to test substances for their possible inhibitory effect on polymerases. The decrease of the known polymerase activity upon addition of the substance then serves as a measure of inhibition and indicates a possible therapeutic use of the substance as an anti-bacterial or anti-viral agent.

Another subject manner of the invention is a method of detecting HIV, said method being based upon the method of determining polymerases. Then a lysate of a sample in which HIV is expected to be present is prepared.

a template ribonucleic acid, at least one detectable and one immobilizable mono-deoxyribonucleoside triphosphate and additives are added to this lysate, after incubation, the mixture is transferred into a vessel which selectively and essentially completely binds the immobilizable mononucleotide and immobilizable nucleotide incorporated.

excess detectable mononucleoside triphosphate is separated and the bound detectable mononucleotide is detected.

The first incubation is preferably carried out in the presence of a primer since the HIV-RT is a primer-dependent type-Ill polymerase. The incubation of the mixture could also take place in the vessel which itself is capable of binding.

This method applies analogously to the detection of other viruses connected to a polymerase. In this case a virus isolate, e.g. a pellet, may serve as sample.

Yet another subject matter is a method of detecting an antibody to a polymerase by incubating the sample containing the antibody to be detected with a template nucleic acid, a detectable mononucleoside triphosphate and the polymerase, separating the synthesized nucleic acid from the detectable mononucleoside triphosphate and detecting the detectable nucleotides contained in the nucleic acid, whereby the incubation mixture contains an additional immobilizable mononucleoside triphosphate and the incubation mixture is or is brought in contact with a solid phase which is able to selectively and essentially completely bind the immobilizable mononucleoside triphosphate and the nucleic acid in which the immobilizable mononucleotide is incorporated.

This process is based on the detection of polymerase activity according to the above invention. The reaction mixture thereof exhibits a certain polymerase activity. Said polymerase activity is compared the one present after addition of the sample which is expected to contain an antibody to this polymerase. If an antibody that is directed against this polymerase is present, the activity will be lower as compared to the activity with no antibody present. The sample material used may be blood, serum, an isolate, a cell culture supernatant or the like.

Therefore, the quantity and the type of reagents used essentially corresponds to those used in method of detecting polymerases. The concentration of the polymerase also depends upon the quantity of the antibody to be detected. However, the expert can find a suitable dilution by running a few tests for this purpose beforehand. The detection range for the method of detecting a polymerase according to the invention may serve as a reference in this case.

Further, it can be advantageous to eliminate the polymerase activity originally present in antibody-containing sample prior to adding the polymerase. Other common reaction conditions are known to the expert, e.g., from J. Clin. Microbiology. (1989). Vol. 27, 7, pp. 1453–1455 and from AIDS Research and Human Retroviruses. (1989). Vol 5, pp. 535–540.

The detection of antibodies to type II or type III polymerases requires an additional corresponding primer.

In a preferred embodiment of the method of detecting antibodies to HIV-RT, the template nucleic acid, biotinylated dUTP (EP-A-0 063 879) as immobilizable mononucleoside triphosphate and digoxigenin-labelled dUTP (WO 89/06698) as detectable mononucleoside triphosphate and a defined quantity of polymerase, e.g. reverse transcriptase, which is obtained from virus lysate or, preferably, by means of genetic engineering, are directly incubated with the serum to be analyzed for appr. 60–90 min at 37° C. After incubation the mixture is transferred into a streptavidin-coated cuvette. After incubation for appr. 60 min, the liquid is discarded and the cuvette is rinsed with a wash solution. Then a solution of POD-labelled antibodies to digoxigenin is added. The liquid is again discarded after appr. 60 min and the cuvette is again rinsed. Then, an ABTS ® solution is added and the coloration is measured at appr. 405 nm.

In the method of the invention, the quantity or the presence of detectable mononucleotide at the solid phase follows from the quantity or the absence of the antibody to the polymerase. A quantitative evaluation is, for example, possible with the aid of a calibration curve obtained with samples that contain a known amount of antibody.

If the conditions under which the individual polymerases or types of polymerases incorporate detectable and immobilizable mononucleotide vary, it is possible to differentiate between antibodies to individual polymerases and between antibodies to types of polymerases. The method of the invention is, hence, a selective method. It is, for example, possible to determine antibodies to polymerases of the one type in the presence of antibodies to the other type.

The method of the invention can, for example, be used for tile detection of an infection with a microorganism which contains a polymerase or contains information for the production of a polymerase, e.g. viruses such as the HIV. The method has the same advantages as the method of detecting polymerase activity, i.e. it is easy, rapid, reliable and more sensitive than the known methods. It is an additional advantage of the method that is does not require tedious IgG-preparations. Serum can be directly used as a sample.

Yet another subject matter of the invention is a method of detecting a promoter sequence comprising the following steps:

incubation of a sample containing the promoter sequence to be detected with a detectable mononucleoside triphosphate and a polymerase which requires the promoter sequence to initiate the polymerase reaction, separation of the synthesized nucleic acid from the detectable mononucleoside triphosphate and detection of the detectable nucleotides contained in the nucleic acid, whereby the incubation mixture contains an additional immobilizable mononucleoside triphosphate and the incubation mixture is or is brought in contact with a solid phase which is able to selectively and essentially completely bind the immobilizable mononucleoside triphosphate and the nucleic acid in which the immobilizable mononucleotide is incorporated.

This method is also based on the determination of polymerase activity in accordance with the invention. However, this method is distinguished from the latter in that a given amount of polymerase is added whereas template nucleic acid is not added in addition to the nucleic acid which is present in the sample to be detected and may contain the promoter sequence. If a promoter is present that is able to initiate the polymerase which was added, the polymerase reaction will occur and labelled nucleic acids can be detected. Promoters which can be detected include the SP6. the T7- and the T3-promoters. The respective polymerases, i.e. the SP6-RNA-polymerase, the T7-RNA-polymerase, and the T3-DNA-polymerase, are then used. The test is specific for the respective promoter. In molecular biology, such tests are advantageously used, for example, in the detection of nucleic acid constructs. The preferred sample is a DNA isolate.

The concentration values and the conditions for the individual reagents basically depend upon the values given in the method of determining polymerase in accordance with the invention.

In a preferred embodiment of the invention, a sample is reacted with biotinylated dUTP (EP-A-0 063 879) as immobilizable and digoxigenin-labelled dUTP (WO 89/06698) as detectable mononucleoside triphosphate and with a polymerase which is specific for the promoter. After incubation at appr 35° C. for 90 min, the mixture is transferred into a streptavidin-coated cuvette. After incubation for appr. 60 min. the liquid is discarded and the cuvette is rinsed with a wash solution. Then a solution of POD-labelled antibodies to digoxigenin is added. After appr. 60 min. the liquid is again discarded and the cuvette is rinsed once more. Then, an ABTS ® solution is added and the coloration is measured at appr. 405 nm.

In the method of the invention, the strength or the presence of a promoter for the polymerase or the type of polymerase follows from the quantity or the presence of detectable mononucleotide at the solid phase.

If the conditions for incorporating detectable and immobilizable mononucleotide differ for the individual polymerases or polymerase subtypes, it is possible to differentiate between individual promoters. The method of the invention is, hence, a selective method. It is, for example, possible to determine promoters of one polymerase subtype in the presence of promoters of another polymerase subtype. Eukaryote polymerases of type I exist in different subtypes (RNA-pol I, II, III) which recognize different promoter types. And each particular polymerase subtype in rum recognizes, in dependency upon additional factors, different promoters.

Yet another subject matter of the invention is a reagent kit for the detection of antibodies to a polymerase. Said reagent kit contains a template nucleic acid, at least one detectable and at least one immobilizable mononucleoside triphosphate and a polymerase against which the antibody to be detected is directed. Preferred further components are additives and, optionally, a vessel or any other solid phase which selectively and essentially completely binds the immobilizable mononucleoside triphosphate and the nucleic acids containing the latter. In a preferred manner, at least the polymerase is available in a separate container.

BRIEF DESCRIPTION OF THE DRAWINGS

FIG. 1 shows the percentage of RT-inhibition (abscissa) by anti-HIV-positive and anti-HIV-negative sera (1:40) for two different virus lysate concentrations.

Figure 2:
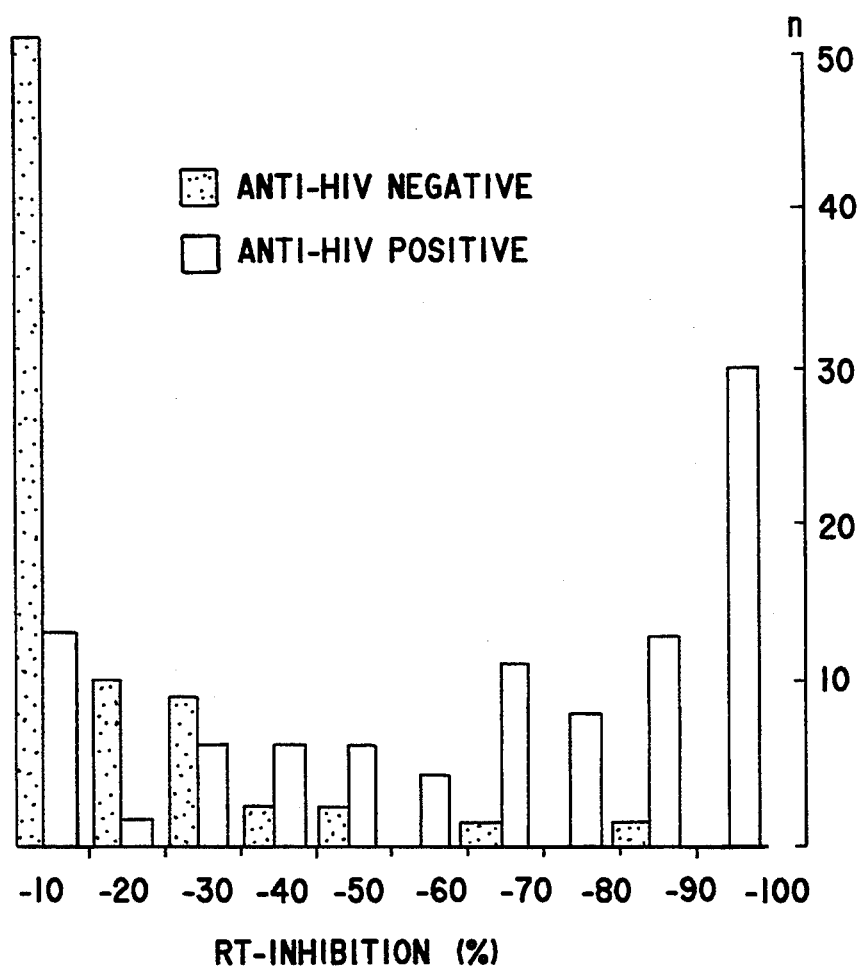
FIG. 2 shows the percentage of RT-inhibition (abscissa) by anti-HIV-positive and anti-HIV-negative sera ( 1: 40) for recombinant RT (appr. 1:27000).

n in FIGS. 1 and 2 represents the number of sera.

The following examples explain the invention in greater detail:

EXAMPLE 1

Detection of HIV a) Preparation of pelleted HIV-virus

2–3 ml of cell-free supernatant of HIV-virus cultures or virus isolation solutions are obtained. A subsequent ultracentrifugation at 20 000 g for a period of 2 hours leads to the formation of a pellet of cellular organelles and (in a positive case) virus particles.

b) Lysis of the pelleted virus

The pelleted virus is disolved in 40 µl lysis buffer.
Lysis buffer:
1,4-dithioerythrite (DTT, Merck, Darmstadt) 2.5 mM;
EDTA (Merck, Darmstadt) 0.75 mM;
KCl (Merck, Darmstadt) 80 mM;
Tris HCl (Boehringer Mannheim) 50 mM; pH 8.0 (22° C.)
Triton ®X-100 (Sigma, Saint Louis) 0.5%

Alternatively, it is also possible to add 5 µl of an eightfold concentrated lysis buffer to 35 µl virus containing supernatant.

At 2° C. this virus lysate can be stored for about one week without significant decrease in activity (protect lysate from drying out).

c) Incubating/polymerase reaction

20 µl of a solution of the following composition are added to the above lysate:
DTT 10 mM;
KCl 290 mM:
$MgCl_2$ 30 mM;
dTTP 8.3 µM;
Biotin-16-dUTP (Boehringer Mannheim, Cat. No. 1 093 070) 125 nM;
DIG-11-dUTP (Boehringer Mannheim, Cat. No. 1 093 088) 2.5 µM;
Polyadenylic acid. Pentadecathymidylic acid (Poly A)-$(dT)_{15}$,
(Boehringer Mannheim, Cat. No. 108 677) 700 U/1, [35 µg/ml];
TrisxHCZ 50 mmol/1. pH 8.0 (22° C.)

The mixture is incubated at 35° C. for a period of 90 min. to 24 hours and even longer depending on the desired test sensitivity.

d) Isolation of the reaction products

After incubating, the reaction mixture is transferred into the wells of a streptavidin-coated 96-well-ELISA plate (manufactured according to EP-A-0 344 578, capacity appr. 20 ng biotin/ml, i.e. in 60 μl appr. 1.2 ng biotin) and then incubated for 60 min. at 35° C.

e) Washing

The wells are then washed 5 times with a wash solution (sodium chloride 0.85 mol/l). The solution still remaining in the wells is then removed by tapping on the plate.

f) Incubation with POD-labelled anti-digoxigenin antibodies

200 μl of a conjugate solution of the following composition are pipetted into each of the wells: anti-digoxigenin-POD (Fab fragments, Cat. No. 1 207 733 Boehringer Mannheim) 200 U/l;
Tween 20 0.5 %
Sodium chloride 0.85 M in 0.1 mol/l sodium phosphate buffer pH 7.5.
The conjugate solution is decanted after 60 min. and the wells are washed 5 times with a wash solution (NaCL 0.85 M).

g) Colorimetric reaction

200 μl substrate solution (ABTS ® (2'2-Azino-di-[3-ethylbenzthiazolinsulfonate (6))][sic] 1 g/l in ABTS ® buffer (Cat. No. 1 112 597. Bothringer Mannheim) are pipetted into each of the wells. After allowing the reaction to occur for another 60 min. at 35° C., the coloration is measured in a photometer at 405 nm against 450 nm.

h) Sensitivity of the tests

The sensitivity of the method of the invention was tested with serial dilutions of aliquots of a positive control (lysate of pelleted HIV-I-particles from appr. 2 ml supernatant of a well producing continuous culture of permanent T cells).

TABLE 1

| Virus dilution | OD 405 nm | Virus dilution | OD 405 nm |
| --- | --- | --- | --- |
| 1:5 | >2.500 | 1:25 | 1.900 |
|  | >2.500 |  | >2.500 |
|  | >2.500 |  | >2.500 |
|  | >2.500 |  | >2.500 |
|  | >2.500 |  | 1.847 |
|  | >2.500 |  | 1.691 |
|  | >2.500 |  | >2.500 |
|  | >2.500 |  | 1.935 |
| 1:50 | 0.730 | 1:125 | 0.602 |
|  | 0.868 |  | 0.633 |
|  | 0.793 |  | 0.599 |
|  | 0.880 |  | 0.613 |
|  | 0.812 |  | 0.506 |
|  | 0.838 |  | 0.496 |
|  | 0.769 |  | 0.453 |
|  | 0.990 |  | 0.455 |
| 1:250 | 0.350 | 1:500 | 0.243 |
|  | 0.348 |  | 0.228 |
|  | 0.340 |  | 0.274 |
|  | 0.404 |  | 0.252 |
|  | 0.307 |  | 0.247 |
|  | 0.308 |  | 0.230 |
|  | 0.242 |  | 0.163 |
|  | 0.245 |  | 0.147 |
| Negative control | OD 405 nm | Blank | OD 405 nm |
| 1:2 | 0.130 |  | 0.072 |
|  | 0.160 |  | 0.075 |
|  | 0.138 |  | 0.068 |
|  | 0.119 |  | 0.090 |
|  | 0.133 |  | 0.083 |
|  | 0.187 |  | 0.073 |

TABLE 1-continued

|  |  |
| --- | --- |
| 0.121 | 0.065 |
| 0.183 | 0.071 |

OD = Optical density, measured at 405 nm against 450 nm.
Blank = Optical density of the non-reacted substrate.

The above listed measured values are obtained in a minimum of four experiments carried out on different days. Between the tests the reaction mixtures used were stored at −20° C. At least two batches prepared on different days were used. A maximum signal (OD>2.5) occured regularly up to a dilution of 1:5 in some test runs even up to a dilution of 1:25. With a continuous decrease of the signal and a simultaneous increase of dilution, the detection limit of the reverse transcriptase is reached at a dilution of appr. 1:500 after a reaction time of 90 min. For a reaction time of 24 hours, the limit is at a dilution of 1:3000 to 1:7500 (6 to 15 times more sensitive). The deviations between the OD-values in the different test runs are typically at a factor smaller than 2. Compared to a conventional method, the new test with a reaction time of 90 min. is at least as sensitive as conventional methods and is distinguished by a more simple handling. Further, as compared to conventional methods, this specifity of the method in accordance with the invention allows extending the reaction time to at least 24 hours and, hence, obtaining a considerably higher sensitivity. Even samples that are massively contaminated with hemoglobin from lysated erythrozytes or with bacteria do not show blanks which exceed the limit. In a direct comparison of various virus isolation solutions (pellet of appr. 3 ml supernatant), the new method convinced with its high reliability.

EXAMPLE 2

Method of detecting reverse transcriptase and testing samples for their possible inhibitory effect on polymerases As in example 1, this test is based on a test for reverse transcriptase.

a) Sample preparation

The samples to be tested for the presence of inhibitors are usually disolved in concentrations of 1 to 10 mg/l in pure DMSO (dimethyisulfoxide). These stock solutions are the basis for dilutions (usually 20- to 200-fold diluted) by diluting with RT-buffer (50 mM Tris-HCl, pH 7.9:50 mM KCl; 5 mM MgCl$_2$; 1 mM DTT).

b) Incubation

The test is carried out directly in the streptavidin-coated 96-well-ELISA plates (manufactured according to EP-A-0 344 578).
The following solutions are sucessively pipetted into the wells of the plate:
20 μl diluted sample solution or RT-buffer for positive control
20 μl RT-buffer
20 μl template/primer complex consisting of 1 μg RNA-template (HIV-LTR-5'-gag fragment) and 21.3 ng 18-mer DNA-primer of the following sequence: SEQ ID NO 1 (5'-GTCCCTGTTCGGGCGCCA-3'): after incubating both components as a mixture in a 50-fold concentrated form at 66.5° C. in a water bath and cooling the mixture slowly down to 30° C., said mixture is 10-fold diluted with RT-buffer.

20 μl HIV-1 RT is reached according to a known process cloned and expressed in E.coli purified to homogenity (Heterodimer, p66/p51, Science (1986), 231:1289–1291) and dissolved in a concentration of 1 μg/ml in RT-buffer.

20 μl reaction starter solution consisting of
RT-buffer (see above)
5 μM dATP
5 μM dCTP
5 μM dGTP
5 μM Dig-11-dUTP
0.25 μM Biotin-16-dUTP
0.1% Nonidet® P 40 (Pierce, Cat. No. 28324)

The HIV-LTR-5'-gag RNA-fragment of 1078 bases in length, which serves as a template, was prepared according to known procedures by in-vitro transcription with the aid of a T7-RNA-polymerase.

The mixture is then at 37° C. incubated for 1 hour in a water bath in a microtiter plate (capacity for binding biotin appr. 20 ng/ml, i.e. in 100 μl appr. 2 ng biotin) with a flat bottom. This microtiter plate was manufactured in accordance with EP-A-0 344 578. The microtiter plate is covered with an adhesive foil.

c) The well is washed 5 times. each time with 0.3 ml of a wash solution (PBS without Ca and Mg (Cat. No. 210 340 Boehringer Mannheim), Tween 20 (Cat. No. 170-6531, Bio-Rad) 0.05 % (vol/vol)).

d) 100 μl anti-digoxigenin-POD (Fabfragments, Cat. No. 1 207 733 Boehringer Mannheim) contained in a solution of 100 mM Tris-HCl, pH 7.9; 150 mM NaCl are added into each well. Incubation is carried out for 30 min. at room temperature.

e) Each well is washed 5 times with 0.3 ml wash solution for each washing step.

f) 100 μl of the following solution are added into each well: ABTS ® 1 g/l in ABTS ®-buffer (Cat. No. 1 114 497 Boehringer Mannheim) Subsequently, the solution is incubated under shaking for 20 to 30 min. at room temperature and the coloration is then measured at 405 nm in an ELISA-photometer (MR 5000, Dynatech, reference filter 630 nm). A polymerase inihibitor is present if the coloration at 405 nm is slowed down or missing.

EXAMPLE 3

Detection of specific DNA-dependent RNA-polymerase activity and specific promoter sequences for RNA-polymerases on DNA Three DNA-fragments, which contain the promoter for either the SP6-RNA-polymerase, the T7-RNA-polymerase or the T3-RNA-polymerase, are in transcription reactions incubated with a mixture of ribonucleotides. The latter also contains Dig UTP and Bio UTP and either SP6-RNA-polymerase or T7-RNA-polymerase. In both assays where promoter and polymerase specifically match, the nucleotides are, complementary to the DNA, incorporated in an RNA-chain. After incubation the reaction solutions are transferred into the wells of a streptavidin-coated 96 well-ELISA plate. Incorporated and non-incorporated biotin residues will bind to the streptavidin. An RNA-polymerase activity can be detected by detecting the digoxigenin-nucleotides or the digoxigenin-haptens, which are covalently bound to the biotin-nucleotides with the aid of anti-digoxigenin antibodies. Correspondingly, it is possible to detect a specific promoter for a polymerase.

| a) Transcription reaction: | | |
|---|---|---|
| 1 μl | template-DNA (100 ng/μl), | 100 ng |
| 2 μl | Dig-Bio-Nucleotide-Mix 10 × | |
| 0.5 μl | RNAsin (50 U/μl, Cat. No. 799 017, Boehringer Mannheim), | 25 U |
| 2 μl | transcription buffer 10 × | |
| x μl | Phage-RNA-polymerase | (20 U) |
| ad 20 μl | H₂O | |
| 20 μl | | |

Template-DNAs

Plasmides containing the appropriate promoter sequences were cleaved by restriction enzymes and electrophoretically separated on an agarose gel. DNA-fragments which contained a promoter were eluted from the gel and used as template-DNAs.

a) Template with SP6-promoter pSPT18 plasmid (Cat. No. 909 793. Boehringer Mannheim) digested with Eco R I+Ssp I, 951 bp-fragment isolated, length of transcript: 58 b b) Template with T7-prompter pSPT18 plasmid (Cat. No. 909 793, Boehringer Mannhelm) digested with Hind III+Ssp I, 2204 bp-fragment isolated, length of transcript: 61 b c) Template with T3-promoter (control)

pT3T71ac plasmid (Cat. No. 1 014 692, Boehringer Mannheim) digested with Eco RI+Sca I, 1815 bp-fragment isolated, length of transcript: 60 b

| Dig-Bio-Nucleotide-Mix 10 ×: | | |
|---|---|---|
| 5 μl | 100 mM ATP | 10 mM |
| 5 μl | 100 mM GTP | 10 mM |
| 5 μl | 100 mM CTP | 10 mM |
| 3.25 μl | 100 mM UTP | 6.5 mM |
| 8.75 μl | 1 mM Bio-11-UTP | 175 nM |
| 16.5 μl | 10 mM Dig-11-UTP | 3.3 mM |
| 6.5 μl | H₂O | |
| 50 μl | | |
| Transcription buffer 10 ×: | | |
| 400 μl | 1M Tris/HCl pH 7.9 | 400 mM |
| 60 μl | 1M MgCl₂ | 60 mM |
| 100 μl | 1M DTT | 100 mM |
| 20 μl | 1M Spermidin | 20 mM |
| 420 μl | H₂O | |
| 1 ml | | |

Phage-RNA-polymerases

SP6-RNA-polymerase, Cat. No. 810 266, Boehringer Mannheim

T7-RNA-polymerase, Cat. No. 881 767, Boehringer Mannheim

As DNA with a spermidin concentration exceeding 4 mM can precipitate, the 10 x-transcription buffer, was added immediately before the addition of the enzymes [Krieg, P. A., Melton, D. A. (1987) Meth. Enzym. 1551. H₂O was treated with DEPC (diethylpyrocarbonate) to inactivate RNAses.

Incubation for 2 hours at 30° C. [after Krieg, P. A. (1990): Nucl. Acids Res. 18, 6463].

b) Binding of the transcripts to the streptavidin in microtiter plates

The transcription reactions were filled up to 100 μl with 80 μl TE (10 mmol/l TrisHCl, 1 mmol EDTA, pH 8.0). Portions of 20 μl of the diluted transcription reactions were pipetted into the flat-bottom wells of a streptavidin-coated 96-well-Elisa plate (manufactured according to EP-A-0 344 587) and 180 μl of a 0.05 % (vol/vol) Tween 20 solution were added. During all following binding and reaction steps, the plates were covered with lids (Nunc, Cat No. 263339).

Binding is carried out at 37° C. under shaking for 1 hour.

Non-bound reaction components are removed in 6 washing steps with 300μl of a 0.9% NaCl-solution used in each step.

c) Detection with anti-digoxigenin-antibody conjugate and color reaction

As described with respect to example 1,200 μl anti-digoxigenin-POD (200 U/I, Cat. No. 1207733 Boehringer Mannheim) are added. After 60 minutes, 6 washing steps are carried out, using 0.9% NaCl solution in each step. As was also desribed with respect to example 1, 200 Ill substrate solution (ABTS ®) are incubated in the wells at 37° C. for 5 to 60 minutes and the coloration is measured in a photometer at 405 nm.

EXAMPLE 4

Detection of antibodies to HIV-RT in patient sera, said antibodies having an inhibitory effect on the funtion of the RT This detection serves as a prognostic factor for an HIV infection and may serve to distinguish between different variants of HIV (HIV 1 and HIV 2).

10 μl diluted serum (1:10 in lysis buffer, see example 1) are added to 30 μl polymerase (obtained from virus lysate or genetically engineered reverse transcriptase), diluted in 1xconcentrated lysis buffer, and incubated for 60–90 minutes at 35° C. 20μl of the reaction solution (as described under c in example 1) are then added and incubated at 35° C. for 24 hours. The remaining procedure corresponds to the one described in example 1. If the sample contains antibodies that inhibit the function of the reverse transcriptase, the signal will either be suppressed or partly reduced. Serum sample without RT-inhibiting antibodies will produce a signal that corresponds to the amount of RT used.

a) Pre-tests:

Several tests were carried out to determine optimal serum- and virus concentrations. In these tests, 6 HIV-I-positive and HIV-negative sera diluted 1:32 and 1:64, respectively, were tested with a standard virus lysate diluted 1:250 (lysated HIV-1 from appr. 1 ml supernatant of a well-producing cell culture of HIV-1 infected H9-cells). In another test, three additional HIV-1 -positive and HIV-negative sera diluted to concentrations of 1:32, 1:64 and 1.128, respectively and standard virus lysate dilutions of 1:125, 1:250 and 1:500, respectively, were tested. Additional tests with different dilutions of a preparation of genetically engineered (recombinant) RT (manufactured by Mikrogen, Munich, FRG) were also carried out. The optimal polymerase dilution was found with the aid of sera whose RT-inhibiting capacities had been characterized before the tests were started. Dilutions of appr. 1:25000 of recombinant RT haven proven to be the most suitable.

The resulting values showed a significant inhibition of the RT function with all HIV-1 positive sera whereas the RT function with HIV -negative sera was not impaired. The relative signal suppression was most pronounced at serum dilutions of 1:32 and 1:64. The ideal dilution of our standard virus lysate was found to range between 1:125 and 1:250.

b) Validation of the test principle with patient sera.

Based on the experiences from the pre-tests, 34 HIV-1-positive and 26 HIV-negative sera, each diluted 1:40. were tested in two batches, one with a virus lysate diluted 1:125 and the second with a virus lysate diluted 1:250. The results are listed in FIG. 1. In order to further validate the test principle, a larger number of sera (98 anti-HIV-l-positive sera and 76 anti-HIV-negative sera) has been tested for inhibiting antibodies with recombinant RT (dilution appr. 1:27000). The total result obtained with the recombinant RT is listed in FIG. 2.

c) Test to establish the prognostic value of RT inhibiting antibodies.

From some of the 132 anti-HIV-1-positive sera, we knew the clinical condition of the patient (asymptomatic LAS/ARC, AIDS) and from some we knew the test result obtained with the p24-antigen-ELISA (manufactured by Abbott Laboratories, North Chicago, USA) with serum or plasma. In a third group, the reaction pattern in the Western blot (WB) can be used to differentiate between diffrerent conditions: shortly after seroconversion (early infection), patients with insignificant antibody profile, beginning drecrease of the anti-p24 level and late stage. To test the prognostic value of RT-inhibiting serum antibodies, the proportion of the sera were RT-inhibition exceeded 50% and the mean RT-inhibition were calculated in a comparison of all groups (see Table 2).

TABLE 2

Prognostic value of RT-inhibiting antibodies in comparison to acknowledged prognostic parameters (p24-antigenemia, clinical rating, WB-antibody profile).

| | number tested | patients with RT-inhibition >50% | corresponds to % with RT-inhibition >50% | average RT-inhibition in % |
|---|---|---|---|---|
| p24-antigen positive | 15 | 10 | 67 | 60,9 |
| p24-antigen negative | 38 | 34 | 89 | 77.3 |
| asymptomatic | 29 | 25 | 86 | 79.1 |
| LAS/ARC | 10 | 9 | 90 | 78.3 |
| AIDS | 13 | 7 | 54 | 44.4 |
| early infection | 5 | 2 | 40 | 44.0 |
| WB normal | 97 | 79 | 81 | 72.6 |
| weak anti-p24 | 9 | 6 | 67 | 65.5 |
| WB late stage | 16 | 7 | 44 | 45.2 |

EXAMPLE 5

Detection of DNA-dependent DNA-polymerase activity

Klenow-polymerase is incubated in a random primed labelling reaction with a thermally denatured DNA fragment and a mixture of hexamers consisting of hexamers of all possible sequences that may serves as primers. In addition to unlabelled nucleotides, the polymerase also incorporates DIGdUTP and BiodUTP. The double-labelled DNA so produced by polymerase activity can in turn be quantitatively determined in streptavidin-coated ELISA plates.

a) Reaction mixture

2 µb of a DNA fragment of 356 bp in length are for 10 minutes and at 95° C. denatured in 15 µl H₂O and then immediately placed on ice. The following is pipetted to these 15 µl:

2 µl Hexanucleotide Mixture in 10x reaction buffer (from Random Primed DNA Labelling Kit, Cat. No. 1004760, Boehringer Mannheim)

2 µl 10x nucleotide-Mix

1 µl Klenow-enzyme (from Random Primed DNA Labelling Kit, Cat. No. 1004760, Boehringer Mannheim)

| 10 × Nucleotide-Mix: | dATP | 2 | mM |
|---|---|---|---|
| | dCTP | 2 | mM |
| | dGTP | 2 | mM |
| | DTTP | 1.75 | mM |
| | DIGdUTP | 0.25 | mM |
| | BiodUTP | 125 | nM |

The reaction mixture is incubated for 3 hours at 37° C. and then diluted 1:10 with TE buffer (10 mM Tris, I mM EDTA).

A control reaction is subject to an identical procedure except that the mixture does not contain BiodUTP.

b) Binding of the reaction products to streptavidin in microtiter plates and detection thereof Portions of 2 µl and 6 µl of the diluted reaction mixture containing 20 ng and 60 ng, respectively, of the DNA fragment used to the labelling reaction, contained in 200 µl TE-buffer, are transferred into streptavidin-coated microtiter plates and incubated for one hour at 37° C.

The plates are then washed three times with 300 µl PBS-buffer with 0.5 % (vol/vol) Tween 20.

Subsequently, 200 µl anti-digoxigenin-POD (150 mU/ml, Cat. No. 1207733, Boehringer Mannheim) are added. After one hour three more washing steps, each with 300 µl PBS buffer with 0.5% (vol/vol) Tween 20, are carried out. Corresponding to the preceding examples, 200 µl ABTS ®-substrate solution are then added and the coloration is measured at 405 nm after an incubation time of 30 min.

| | Result | | | |
|---|---|---|---|---|
| | diluted reaction mixture without BiodUTP | | diluted reaction mixture with BiodUTP | |
| | 2 µl | 6 µl | 2 µl | 6 µl |
| | −0.013 | 0.073 | 0.285 | 1.094 |

Sequence protocol:

SEQ ID NO: 1

| Length of sequence: | 18 bases |
|---|---|
| Type of sequence: | nucleotide |
| Type of strand: | single strand |
| Topology: | linear |
| | GTCCCTGTTC GGGCGCCA |

We claim:

1. Method for detecting polymerase activity in a sample comprising the steps of:

a) combining a sample suspected of containing a polymerase with a template nucleic acid and mononucleoside triphosphates to form an incubation mixture, wherein said mononucleoside triphosphates include a detectable mononucleoside triphosphate and a separate immobilizable mononucleoside triphosphate, wherein said immobilizable mononucleoside triphosphate is now used as a detectable label, b) incubating said incubation mixture to incorporate the detectable mononucleoside triphosphate and the immobilizable mononucleoside triphosphate into a newly formed nucleic acid, c) contacting said incubation mixture with a solid phase which selectively binds the immobilizable mononucleoside triphosphate and the newly formed nucleic acid in which the immobilizable mononucleoside triphosphate is incorporated, d) separating said newly formed nucleic acid from any unincorporated detectable mononucleoside triphosphate, and e) detecting the detectable mononucleoside triphosphate incorporated into the newly formed nucleic acid as a measure of the polymerase activity.

2. Method according to claim 1, wherein the template nucleic acid is a DNA which contains a promoter which is specific for the polymerase and the mononucleoside triphosphates are ribonucleoside triphosphates.

3. Method according to claim 1, wherein the template nucleic acid is a DNA and the mononucleoside triphosphates are deoxyribonucleoside triphosphates.

4. The method according to claim 3, further comprising adding an oligonucleotide to the incubation mixture, wherein said oligonucleotide is complementary to a part of the template nucleic acid.

5. Method according to claim 1, wherein the template nucleic acid is an RNA and the mononucleoside triphosphates are deoxyribonucleoside triphosphates.

6. Method according to claim 1, wherein the template nucleic acid is an RNA which contains a primer structure and the mononucleoside triphosphates are ribonucleoside triphosphates.

7. Method according to claim 1, further comprising adding a polymerase inhibitor to the incubation mixture formed in step a).

8. Method according to claim 1, wherein the polymerase to be detected is a reverse transcriptase.

9. Method according to claim 8, wherein the reverse transcriptase is Human Immunodeficiency Virus (HIV) reverse transcriptase.

10. Method for screening for the possibility of Human Immunodeficiency Virus (HIV) in a sample comprising the steps of:
a) preparing a lysate from a sample in which HIV is suspected to be present,
b) adding to the lysate a template ribonucleic acid, and monodeoxyribonucleoside triphosphates to form a mixture, wherein said monodeoxyribonucleoside triphosphates include at least one detectable and at least one separate immobilizable monodeoxyribonucleoside triphosphate, wherein said immobilizable mononucleoside triphosphate is not used as a detectable label,
c) incubating the mixture to incorporate the detectable monodeoxyribonucleoside triphosphate and the immobilizable monodeoxyribonucleoside triphosphate into a newly formed nucleic acid,
d) then transferring the mixture into a vessel which selectively binds the immobilizable monodeoxyribonucleoside triphosphate and the newly formed nucleic acid in which the immobilizable monodeoxyribonucleoside triphosphate is incorporated,
e) separating any excess detectable monodeoxyribonucleoside triphosphate from the vessel, and
f) detecting any detectable mononucleotide bound to said vessel as an indication of the possibility of the presence of Human Immunodeficiency Virus (HIV).

11. The method according to claim 10, wherein a primer is added to the mixture before incubation.

12. Method for determining the inhibitory effect of a substance on polymerase activity comprising the steps of:
a) combining the substance with a polymerase in the presence of a template nucleic acid and mononucleoside triphosphates to form an incubation mixture, wherein said mononucleoside triphosphates includes at least one detectable and at least one separate immobilizable mononucleotide triphosphate, wherein said immobilizable mononucleoside triphosphate is not used as a detectable label,
b) incubating said incubation mixture to incorporate the detectable mononucleoside triphosphate and the immobilizable mononucleoside triphosphate into a newly formed nucleic acid,
c) separating the newly formed nucleic acid from any non-incorporated detectable mononucleoside triphosphates by contacting said newly formed nucleic acid with a solid phase which selectively binds the immobilizable mononucleoside triphosphate and the newly formed nucleic acid in which the immobilizable mononucleotide is incorporated, and
d) detecting the detectable mononucleoside triphosphate incorporated into the newly formed nucleic acid as an indication of the inhibitory effect of a substance on polymerase activity.

13. Method for detecting an antibody to a polymerase in a sample comprising the steps of:
a) combining the sample containing the antibody to be detected with a template nucleic acid, mononucleoside triphosphates and a polymerase to form an incubation mixture, wherein said mononucleoside triphosphates include a detectable mononucleoside triphosphate and a separate immobilizable mononucleoside triphosphate, wherein said immobilizale mononucleoside triphosphate is not used as a detectable label,
b) incubating the incubation mixture to incorporate the detectable mononucleoside triphosphate and the immobilizable mononucleoside triphosphate into a newly formed nucleic acid,
c) contacting the incubation mixture with a solid phase which selectively binds the immobilizable mononucleoside triphosphate including the immobilizable mononucleoside triphosphate which is incorporated in the newly formed nucleic acid,
d) separating the newly formed nucleic acid from any remaining detectable mononucleoside triphosphate and
e) detecting the detectable mononucleoside triphosphate incorporated into the newly formed nucleic acids as an indication of the presence of said antibody.

14. Method for detecting a promotor sequence in a sample comprising the steps of:
a) combining a sample suspected of containing the promotor sequence to be detected, with a detectable mononucleoside triphosphate, a separate immobilizable mononucleoside triphosphate and a polymerase to form an incubation mixture, wherein said polymerase requires the promotor sequence to initiate a polymerase reaction, and wherein said immobilizable mononucleoside triphosphate is not used as a detectable label,
b) incubating said incubation mixture to incorporate the detectable mononucleoside triphosphate and the immobilizable mononucleoside triphosphate into a newly formed nucleic acid,
c) contacting the incubating mixture with a solid phase which selectively [and essentially completely]binds the immobilizable mononucleoside triphosphate and the newly formed nucleic acid in which the immobilizable mononucleoside triphosphate is incorporated,
d) separating the newly formed nucleic acid from any remaining detectable mononucleoside triphosphate, and
e) detecting the detectable mononucleoside triphosphates incorporated into the newly formed nucleic acid as an indication of the presence of a promotor sequence.

* * * * *